(12) United States Patent
Azijn et al.

(10) Patent No.: US 8,076,062 B2
(45) Date of Patent: Dec. 13, 2011

(54) MUTATIONAL PROFILES IN HIV-1 PROTEASE CORRELATED WITH PHENOTYPIC DRUG RESISTANCE

(75) Inventors: Hilde Azijn, Leuven (BE); Marie-Pierre T. M. M. G De Bethune, Everberg (BE); Johan Hendrika Jozef Vingerhoets, Wijnegem (BE)

(73) Assignee: Tibotec Pharmaceuticals Ltd., Co Cork (IE)

( * ) Notice: Subject to any disclaimer, the term of this patent is extended or adjusted under 35 U.S.C. 154(b) by 0 days.

(21) Appl. No.: 12/261,475

(22) Filed: Oct. 30, 2008

(65) Prior Publication Data

US 2009/0061420 A1    Mar. 5, 2009

Related U.S. Application Data

(62) Division of application No. 10/518,525, filed as application No. PCT/EP03/50280 on Jun. 30, 2003, now Pat. No. 7,473,524.

(60) Provisional application No. 60/393,005, filed on Jul. 1, 2002.

(51) Int. Cl.
  C12Q 1/00        (2006.01)
  C12Q 1/70        (2006.01)
  C12Q 1/68        (2006.01)

(52) U.S. Cl. .............................................. 435/4; 435/5

(58) Field of Classification Search .................... None
  See application file for complete search history.

(56) References Cited

U.S. PATENT DOCUMENTS

| | | | |
|---|---|---|---|
| 327,742 | A | 10/1885 | Uren |
| 5,631,128 | A | 5/1997 | Kozal et al. |
| 5,650,268 | A | 7/1997 | Kozal et al. |
| 5,856,086 | A | 1/1999 | Kozal et al. |
| 6,221,578 | B1 | 4/2001 | de Bethune et al. |
| 6,528,251 | B2 | 3/2003 | de Bethune et al. |
| 7,058,616 | B1 | 6/2006 | Larder et al. |
| 7,217,506 | B2 | 5/2007 | De Meyer et al. |
| 7,292,944 | B2 | 11/2007 | Larder et al. |
| 7,473,524 | B2 | 1/2009 | Azijn et al. |
| 7,494,768 | B1 | 2/2009 | Hertogs et al. |
| 2003/0190603 | A1 | 10/2003 | Larder et al. |
| 2004/0073378 | A1 | 4/2004 | Dehertogh et al. |
| 2005/0124744 | A1 | 6/2005 | Demain |
| 2005/0233312 | A1 | 10/2005 | De Meyer et al. |
| 2008/0286754 | A1 | 11/2008 | Dehertogh et al. |
| 2009/0352626 | | 1/2009 | Hertogs et al. |
| 2009/0162867 | A1 | 6/2009 | Hertogs et al. |

FOREIGN PATENT DOCUMENTS

| | | |
|---|---|---|
| CA | 2029123 | 5/1991 |
| EP | 406985 A2 | 1/1991 |
| EP | 0 422 762 | 4/1991 |
| EP | 0 428 000 | 5/1991 |
| EP | 0 518 557 | 12/1992 |
| EP | 0 824 148 | 2/1998 |
| EP | 0 104 445 | 10/2001 |
| EP | 0 106 360 | 12/2001 |
| EP | 1605064 A1 | 12/2005 |
| JP | 2002-199890 | 7/2002 |
| WO | WO 96/08580 | 3/1996 |
| WO | 97/27332 A1 | 7/1997 |
| WO | 97/27480 A1 | 7/1997 |
| WO | WO 97/27319 A1 | 7/1997 |
| WO | 99/67428 A2 | 12/1999 |
| WO | WO 99/67417 | 12/1999 |
| WO | WO-9961658 A1 | 12/1999 |
| WO | WO-9961666 A1 | 12/1999 |
| WO | WO-9967427 A1 | 12/1999 |
| WO | 00/73511 A1 | 12/2000 |
| WO | 00/78994 A1 | 12/2000 |
| WO | 00/78996 A1 | 12/2000 |
| WO | 01/79540 A2 | 10/2001 |
| WO | 01/81624 A1 | 11/2001 |
| WO | 01/95230 A2 | 12/2001 |
| WO | 02/22076 A2 | 3/2002 |
| WO | 02/33402 A2 | 4/2002 |
| WO | 02/38792 A2 | 5/2002 |
| WO | 02/083657 A2 | 10/2002 |
| WO | 2004/022523 A2 | 3/2004 |

OTHER PUBLICATIONS

Yin et al. Overcoming HIV drug resistance through rational drug design based on molecular, biochemical, and structural profiles of HIV resistance. Cellular Molecular Life Sciences 2006, vol. 63, pp. 1706-1724.*

Yee et al. Prospects for gene therapy using HIV-based vectors. Somatic Cell and Molecular Genetics, Nov. 2001, vol. 26, No. 1/6, pp. 159-174.*

In the U.S. Patent and Trademark Office, Non-Final Office Action in re: U.S. Appl. No. 10/518,525, dated May 10, 2006, 9 pages.

In the U.S. Patent and Trademark Office, Final Office Action in re: U.S. Appl. No. 10/518,525, dated Feb. 7, 2007, 10 pages.

In the U.S. Patent and Trademark Office, Final Office Action in re: U.S. Appl. No. 10/518,525, dated Oct. 18, 2007, 6 pages.

In the U.S. Patent and Trademark Office, Non-Final Office Action in re: U.S. Appl. No. 10/519,436, dated Mar. 13, 2006, 11 pages.

In the U.S. Patent and Trademark Office, Non-Final Office Action in re: U.S. Appl. No. 10/519,436, dated Mar. 7, 2007, 14 pages.

In the U.S. Patent and Trademark Office, Non-Final Office Action in re: U.S. Appl. No. 10/519,436, dated Oct. 18, 2007, 8 pages.

(Continued)

*Primary Examiner* — Jeffrey S. Parkin
*Assistant Examiner* — Louise Humphrey
(74) *Attorney, Agent, or Firm* — Patton Boggs LLP

(57) ABSTRACT

The present invention is directed to the field of nucleic acid diagnostics and the identification of base variation in target nucleic acid sequences. More particularly, the present invention relates to the use of such genotypic characterization of a target population of HIV and the subsequent association, i.e., correlation, of this information to phenotypic interpretation in order to correlate virus mutational profiles with drug resistance. The invention also relates to methods of utilizing the mutational profiles of the invention in drug development, i.e., drug discovery, drug design, drug modification, and therapy, treatment design, clinical management and diagnostic analysis.

6 Claims, No Drawings

OTHER PUBLICATIONS

In the U.S. Patent and Trademark Office, Non-Final Office Action in re: U.S. Appl. No. 10/519,436, dated Jun. 30, 2008, 10 pages.
In the U.S. Patent and Trademark Office, Non-Final Office Action in re: U.S. Appl. No. 10/519,436, dated Mar. 4, 2009, 10 pages.
In the U.S. Patent and Trademark Office, Non-Final Office Action in re: U.S. Appl. No. 10/519,436, dated Sep. 17, 2009, 13 pages.
In the U.S. Patent and Trademark Office, Non-Final Office Action in re: U.S. Appl. No. 10/519,035, dated Dec. 16, 2005, 6 pages.
In the U.S. Patent and Trademark Office, Non-Final Office Action in re: U.S. Appl. No. 10/399,920, dated Aug. 25, 2005, 14 pages.
In the U.S. Patent and Trademark Office, Final Office Action in re: U.S. Appl. No. 10/399,920, dated Aug. 4, 2006, 9 pages.
In the U.S. Patent and Trademark Office, Final Office Action in re: U.S. Appl. No. 10/399,920, dated May 2, 2007, 10 pages.
In the U.S. Patent and Trademark Office, Non-Final Office Action in re: U.S. Appl. No. 11/933,747, dated Aug. 7, 2009.
In the U.S. Patent and Trademark Office, Non-Final Office Action in re: U.S. Appl. No. 11/613,584, dated Mar. 12, 2009, 9 pages.
In the U.S. Patent and Trademark Office, Non-Final Office Action in re: U.S. Appl. No. 11/613,584, dated Apr. 15, 2010, 11 pages.
In the U.S. Patent and Trademark Office, Final Office Action in re: U.S. Appl. No. 10/519,436, dated May 11, 2010, 10 pages.
Bacheler et al., "Human Immunodeficiency Virus Type 1 Mutations Selected in Patients Failing Efavirenz Combination Therapy," *Antimicrobial Agents and Chemotherapy*, 2000; 44(9):2475-2484.
Beerenwinkel et al., "Diversity and Complexity of HIV-1 Drug Resistance: A Bioinformatics Approach to Predicting Phenotype from Genotype," *PNAS*, 2002; 99(2):8271-8276.
Clevenbergh et al., "Prevalence of Nonucleoside Reverse Transcriptase Inhibitor (NNRTI) Resistance-Associated Mutations and Polymorphisms in NNRTI-Naïve HIV-Infected Patients," *HIV Clin Trials*, 2002; 3(1):36-44.
Craig et al., "HIV Protease Genotype and Viral Sensitivity to HIV Protease Inhibitors Following Saquinavir Therapy," *AIDS*, 1998; 12:1611-1618.
DeScamps et al., "Line Probe Assay for Detection of Human Immunodeficiency Virus type 1 Mutations Conferring Resistance to Nucleoside Inhibitors of Reverse Transcriptase: Comparison with Sequence Analysis," *Journal of Clinical Microbiology*, 1998;36(7):2143-2145.
Eshleman et al., Analysis of Human Immunodeficiency Virus Type 1 Drug Resistance in Children Receiving Nucleoside Analogue Reverse-Transcriptase Inhibitors plus Nevirapine, Nelfinavir, or Ritonavir (Pediatric AIDS Clinical Trials Group 377), *Journal of Infectious Disease*, 2001; 183:1732-1738.
Fodor, et al., "DNA Sequencing: Massively Parallel Genomics," *Science*, 1997; 277:393-395.
Fukui, T., et al., "Cloning and Analysis of the Poly (3-Hydroxybutyrate-co-3-Hydroxyhexanoate) Biosynthesis Genes of *Aeromonas caviae*", *Journal Baceriology*, 1997; 179(15):4821-4830.
Hertogs et al., "A Novel Human Immunodeficiency Virus Type 1 Reverse Transcriptase Mutational Pattern Confers Phenotypic Lamivudine Resistance in the Absence of Mutation 184V," *Antimicrobial Agents and Chemotherapy*, 2000; 44(3):568-573.
Iversen et al., "Multidrug-Resistant Human Immunodeficiency Virus Type 1 Strains Resulting from Combination Antiretroviral Therapy", *Journal of Virology*, 1996; 70(2):1086-1090.
Japour, et al., "Standardized Peripheral Blood Mononuclear Cell Culture Assay for Determination of Drug Susceptibilities of Clinical Human Immunodeficiency Virus Type 1 Isolates," *Antimicrobial Agents Chemotherapy*, 1993; 37(5):1095-1101.
Kellam et al., "Recombinant Virus Assay: A Rapid, Phenotypic Assay for Assessment of Drug Susceptibility of Human Immunodeficiency Virus Type 1 Isolates," *Antimicrobial Agents and Chemotherapy*, 1994; 38(1):23-30.
Kemp et al., "Analysis of 5000 HIV-1 Clinical Samples Reveals Complex Non-Nucleoside RT Inhibitor Resistance Patterns," *Antiviral Therapy*, 1999; 4(Suppl 1):20.
Kichise et al., "Enhanced Accumulation and Changed Monomer Composition in Polyhydroxyalkanoate (PHA) Copolyester by in Vitro Evolution of *Aeromonas caviae* PHA Synthase," *Applied and Environmental Microbiology*, 2002; 68(5):2411-2419.
Kim et al., "Anti-HIV Type 1 Activity of 3'-Fluoro-3'-Deoxythymidine for Several Different Multidrug-Resistant Mutants," *Aids Research and Human Retroviruses*, 2001; 17(5):401-407.
Korber, et al., "Numbering Positions in HIV Relative to HXB2CG," *Numbering Positions in HIV*, 1998; pp. III102-111.
Kusumi et al., "Human Immunodeficiency Virus Type 1 Envelope Gene Structure and Diversity in Vivo and Cocultivation in Vitro," *Journal of Virology*, 1992; 66(2):875-885.
Larder, et al., "Multiple Mutations in HIV-1 Reverse Transcriptase Confer High-Level Resistance to Zidovudine (AZT)," *Science*, 1989; 246(4934):1155-1158.
Larder et al., "Zidovudine Resistance Predicted by Direct Detection of Mutations in DNA from HIV-Infected Lymphocytes," *AIDS*, 1991; 5:137-144.
Margot et al., "Genotypic and Phenotypic Analyses of HIV-1 in Antiretroviral-Experienced Patients Treated with Tenofovir DF," *AIDS*, 2002; 16:1227-1235.
Mellors, et al., "Mutations in HIV-1 Reverse Transcriptase and Protease Associated with Drug Resistance," *Mutations in RT and Protease*, 1995; pp. III-93-III-105.
Parikh et al., "Mutations in Retroviral Genes Associated with Drug Resistance," *HIV Database Review*, 2000; 106-161.
Patick, et al., "Antiviral and Resistance Studies of AG1343, an orally Bioavailable Inhibitor of Human Immunodeficiency Virus Protease," *Antimicrobial Agents and Chemotherapy*; 1996; 40(2):292-297.
Paulous et al, "A 1 Week, Single-Cycle Protease Inhibitor Resistance Assay," *International Workshop on HIV Drug Resistance, Treatment Strategies and Eradication Session 3*, 1997; Abstract 46.
Pauwels et al., 2nd Annual Workshop on HIV Drug Resistance and Treatment Strategies, Lake Maggiore, Italy, Abstract 51, 1998.
Proudfoot et al., "Novel Non-nucleoside Inhibitors of Human Immunodeficiency Virus Type 1 (HIV-1) Reserve Transcriptase. 4.1 2-Substituted Dipyridodiazepinones as Potent Inhibitors of Both Wild-Type and Cysteine-181 HIV-1 Reverse Transcriptase Enzymes," *Journal of Medical Chemistry*, 1995; 38(24):4830-4838.
Richman, et al., "Nevirapine Resistance Mutations of Human Immunodeficiency Virus Type 1 Selected during Therapy," *Journal of Virology*, 1994; 68(3):1660-1666.
Robinson et al., "HIV Type 1 Protease Cleavage Site Mutations and Viral Fitness: Implications for Drug Susceptibility Phenotyping Assays," *AIDS Research and Human Retroviruses*, 2000; 16(12):1149-1156.
Servais et al., "Genotypic Correlates of Resistance to HIV-1 Protease Inhibitors on Longitudinal Data: The Role of Secondary Mutations," *Antiviral Therapy*, 2002; 6:239-248.
Shafer et al., "Highly Active Antiretroviral Therapy for the Treatment of Infection with Human Immunodeficiency Virus Type 1," *Biomedicine & Pharmacotherapy*, 1999; 53:73-86.
Shafer et al., "Online Comparison of HIV-1 Drug Resistance Algorithms Identifies Rates and Causes of Discordant Interpretations," *Antiviral Therapy*, 2001; 6(Supplement 1):101-102.
Shafer et al., "Human Immunodeficiency Virus Reverse Transcriptase and Protease Sequence Database," *Nucleic Acids Research*, 1999; 27(1):348-352.
Stein et al., "Sequence Analysis of Proviral HIV RT Amplified Directly by a Semi-Quantitative Technique from AZT Treated Patients," *Journal of Medical Virology*, 1994; 44:115-121.
Stuyver et al., "Line Probe Assay for Rapid Detection of Drug-Selected Mutations in the Human Immunodeficiency Virus Type 1 Reverse Transcriptase Gene," *Antimicrobial Agents and Chemotherapy*, 1997; 41(2):284-291.
Watkins et al., "Selection of High-Level Resistance to Human Immunodeficiency Virus Type 1 Protease Inhibitors," *Antimicrobial Agents and Chemotherapy*, 2003; 47(2):759-769.
Condra, Jon ., et al. Genetic Correlates of In Vivo Viral Resistance to Individual Human Immunodeficiency Virus Type 1 Protease Inhibitor. Journal of Virology, Dec. 1996, pp. 8270-8276.
D'Aquila, R., HIV-1 Chemotherapy and Drug Resistance. Clinical and Diagnostic Virology 3 p. 299-316 (1995).

Deeks, S., et al. Correlation of Baseline Phenotypic Drug Susceptibility with 16 Week Virologic Response in a Pilot combination Therapy Study in HIV-infected Patients who Failed Indinavir Therapy. Lake Maggior, Italy 24-27 Jun. 1998.

Eastman, P. Scott, et al. Nonisotopic Hybridization Assay for Determination of Relative Amounts of Genotypic Human Immunodeficiency Virus Type 1 Zidovudine Resistance. Journal of Clinical Microbiology, Oct. 1995, pp. 2777-2780.

Eastman, R., et al. Comparison of Selective Polymerase Chain Reaction Primers and Differential Probe Hybridization of Polymerase Chain Reaction Products for Determination of Relative Amounts of Codon 215 Mutant and Wild-Type HIV-1 Populations, Journal of Acquired Immune Deficiency Syndromes and Human Retrovirology, 9, p. 263-273 (1995).

Eriksson, Bertil F.H., et al. Phosphorylation of 3'-Azido-2',3'-Dideoxyuridine and Preferential Inhibition of Human and Simian Immunodeficiency Virus Reverse Transcriptases by Its 5'-Triphosphate. Antimicrobial Agents ad Chemotherapy, Oct. 1989, pp. 1729-1734.

Fodor, Stephen P.A., et al. Multiplexed Biochemical Assays With Biological Chips. Nature, Aug. 5, 1993, vol. 364, pp. 555-556.

Gingeras, T., et al. Use of Self-Sustained Sequence Replication Amplification Reaction to Analyze and Detect Mutations in Zidovudine-Resistant Human immunodeficiency Virus, Journal of Infectius Diseases 164, p. 1066-74 (1991).

Harada, Shinji, et al. Infection of HTLV-III/LAV in HTLV-I-Carring Cells MT-2 and MT-4 and Application in a Plaque Assay. Department o Virology and Prasitology, Yamaguchi University, Japan, Aug. 9, 1985, p. 563-566.

Hertogs, Kurt, et al. A Rapid Method for Simultaneous Detection of Pheotpic Resistance to Inhibitors of Protease and Reverse Transcriptase in Recombinant Human Immunodeficiency Virus Type 1 Isolates from Patients Treated with Antiretroviral Drugs. Antimicrobial Agents and Chemotherapy, Feb. 1998, pp. 269-276.

Holodniy, M., et al. Determination of Human Immunodeficiency Virus RNA in Plasma and Cellular Viral DNA Genotypic Zidovudine Resistance and Viral Load During Zidovudine-Didanosine combination Therapy. Journal of Virology, vol. 69, No. 6, p. 3510-3516 (Jun. 1995).

Ibanex, Angela, et al. Human Immunodeficiency Virus Type 1 Population Bottleneck During Individual Therapy Causes a Genetic Drift in the quasispecies. Journal of General Virology, 2000, p. 85-95.

Konig, Herbert, et al. Azidothymidine Triphosphate Is an Inhibitor of Both Human Immunodeficiency Virus Type 1 Reverse Transcripatse and DNA Polymerase Gamma. Antimicrobial Agents and Chemotherapy, Dec. 1989, pp. 2109-2114.

Larder, Brendan A., et al. HIV with a Reduced Sensitivity to Zidovudine (AZT) Isolated During Prolonged Therapy. Reports, Mar. 31, 1980, pp. 1731-1734.

Lennerstrand, J., et al. A Method for Combined Immunoaffinity Purification and Assay of HIV-1 Reverse Transcriptase Activity Useful for Crude Samples. Analytical Biochemistry 235, 1996, pp. 141-152.

Miller, Veronica, et al. Patterns of Resistance and Cross-Resistance to Human Immunodeficiency Virus type 1 Reverse Transcriptase Inhibitors in Patients Treated with the Nonnucleoside Reverse Transcripatse Inhibitor Loviride. Antimicrobial Agents and Chemotherapy, Dec. 1998, pp. 3123-3129.

Pauwels, R., et al. Rapid and automated Tetrazolium-Based Colorimetric Assay for the Detection of anti-HIV Compounds, Journal of Virgological Methods, 20 p. 309-321 (1988).

Richmond D., et al. Detection of Mutations Associated with Zidovudine Resistance in Human Immunodeficiency Virus by Use of the Polymerase Chain Reaction. Journal of Infectious diseases vol. 164, p. 10675-1081 (1991).

Rusconi, Stefao, et al. Susceptibility to PNU-140690 (Tipranavir) of Human Immunodeficiency Virus Type 1 Isolates Derived from Patients with Multidrug Resistance to Other Protease Inhibitors. Antimicrobial Agents and Chemotherapy, May 2000, pp. 1328-1332.

Schinazi, R., et al. Mutations in Retroviral Genes Associated with Drug Resistance: 2000-2001 Update. International Antiviral News 8:5 p. 65 (2000).

Toth, Mihaly V., et al. A Simple, Continuous Flurometric Assay for HIV Protease. Int. J. Peptide Protein Res. 36, 1990, pp. 544-550.

Tyagi, Suresh C., et al. Continuous Assay of the Hydrolytic Activity of Human Immunodeficiency Virus-1 Protease. Analytical Biochemistry 200, pp. 143-145 (1992).

Tyagi, Sanjay, et al. Multicolor Molecular Beacons for Allele Discrimination. Nature Biotechnology, Jan. 1998, vol. 16, pp. 49-53.

Vasudevachari, M.B., et al. Emergence of Protease Inhibitor Resistance Mutations in Human Immunodeficiency Virus Type 1 Isolates from Patients and Rapid Screening Procedure for Their Detection. Antimicrobial Agents and Chemotherapy, Nov. 1996, pp. 2535-2541, vol. 40, No. 11.

Vergne, Lurence, et al. Genetic Diversity of Protease and Reverse Transcriptase Sequences in Non-Subtype-B Human Immunodeficiency Virus Type 1 Strains: Evidence of Many Minor Drug Resistance Mutations in Treatment-Naïve Patents. Journal of Clinical Microbiology, Nov. 2000, p. 3919-3925, vol. 38, No. 11.

In the U.S. Patent and Trademark Office U.S. Appl. No. 09/580,491 Advisory Action dated Mar. 7, 2006, 2 pages.

In the U.S. Patent and Trademark Office U.S. Appl. No. 09/580,491 Final Office Action dated Aug. 26, 2003, 8 pages.

In the U.S. Patent and Trademark Office U.S. Appl. No. 09/580,491 Final Office Action dated Jan. 22, 2008, 7 pages.

In the U.S. Patent and Trademark Office U.S. Appl. No. 09/580,491 Final Office Action dated Sep. 12, 2005, 4 pages.

In the U.S. Patent and Trademark Office U.S Appl. No. 09/580,491 Non-Final Office Action dated Dec. 16, 2004, 6 pages.

In the U.S. Patent and Trademark Office U.S. Appl. No. 09/580,491 Non-Final Office Action dated Dec. 23, 2002, 6 pages.

In the U.S. Patent and Trademark Office U.S. Appl. No. 09/580,491 Non-Final Office Action dated Dec. 4, 2001, 7 pages.

In the U.S. Patent and Trademark Office U.S. Appl. No. 09/580,491 Non-Final Office Action dated May 9, 2007, 5 pages.

In the U.S. Patent and Trademark Office U.S. Appl. No. 09/580,491 Non-Final Office Action dated Sep. 26, 2006, 3 pages.

In the U.S. Patent and Trademark Office U.S. Appl. No. 11/933,747 Final Office Action dated Apr. 5, 2010, 8 pages.

In the U.S. Patent and Trademark Office U.S. Appl. No. 12/352,626 Non-Final Office Action dated Jul. 23, 2010, 7 pages.

Abremski et al., "pol protein HIV-1," downloaded from <http://www.ncbi.nlm.nih.gov/protein/AAG03320> 2000: 1-2.

Angarano et al.; "Genotype and Phenotype Resistance: An Overview," *Journal of Biological Regulators and Homeostatic Agents*, 2000; 14:11-14.

Anton et al.; "Comparative Patterns of HIV-1 Genotypic and Phenotypic Resistance Profiles in Gut and Plasma," *3rd International Workshop on HIV Drug Resistance and Treatment Strategies*, 1999; Abstract 86, 4(1).

Bacheler et al.; "Genotypic Correlates of Phenotypic Resistance to Efavirenz in Virus Isolates from Patients Failing Nonnucleoside Reverse Transcriptase Inhibitor Therapy," *Journal of Virology*, 2001; 75(11):4999-5088.

Bakhanashvili et al.; "Mutational studies of human immunodeficiency virus type 1 reverse transcriptase: the involvement of residues 183 and 184 in the fidelity of DNA synthesis," *FEBS Letters*, 1996; 391(3):257-262.

Bally, F. et al.; "Polymorphism of HIV Type 1 Gag p7/p1 and p1/p6 Cleavage Sites: Clinical Significance and Implications for Resistance to Protease Inhibitors," *AIDS Research and Human Retroviruses*, 2000; 16(13):1209-1213.

Balotta et al.; "Prevalence of Transmitted Nucleoside Analogue-Resistant HIV-1 Strains and Pre-Existing Mutations in *pol* Reverse Transcriptase and Protease Region: Outcome After Treatment in Recently Infected Individuals," *Antiviral Therapy*, 2000 5:7-14.

Been-Tiktak et al.; "In-Vitro Selection of HIV-1 Variants Resistant to Non-Nucleoside Reverse Transcriptase Inhibitors in Monocyte-Derived Macrophages," *Journal of Antimicrobial Chemotherapy*, 1997; 40:847-853.

Bloor et al.; "Lamivudine-Resistant HIV-1 Clinical Isolates Lacking the Met184Val Mutation have Novel Polymorphisms in RT," *3rd International Workshop on HIV Drug Resistance and Treatment Strategies*, 1999; Abstract 25, 4(1).

Calvez, V.; "Resistance to Antiretroviral Drugs," *Antiviral Therapy*, 1998; 3(4):5-7.

Casado et al.; "Rate of Non-nucleoside Reverse Transcriptase Inhibitor Resistance Among Patients Failing a Nevirapine Plus Protease Inhibitor-Containing Regimen," $3^{rd}$ *International Workshop on HIV Drug Resistance and Treatment Strategies*, 1999; Abstract 114, 1(1).

Catucci et al.; "Development and Significance of the HIV-1 Reverse Transcriptase M184V Mutation During Combination Therapy with Lamivudine, Zidovudine, and Protease Inhibitors," *Journal of Acquired Immune Deficiency Syndromes*, 1999; 21:203-208.

Chen et al.; "Drug Resistance Mutations as Predictors of Phenotypic Zidovudine Resistance in HIV-1 infection," *AIDS*, 1997; 11(12):1528-1529.

Clotet et al.; "Efficacy and safety of darunavir-ritonavir at week 48 in treatment-experienced patients with HIV-1 infection in POWER 1 and 2: a pooled subgroup analysis of data from two randomised trials," *Lancet*, 2007; 369:1169-1178.

Coakley et al.; "Phenotypic and Genotypic Resistance Patterns of HIV-1 Isolates Derived from Individuals Treated with Didanosine and Stavudine," *AIDS*, 2000; 14:F9-F15.

Condra et al.; "Genotypic or phenotypic susceptibility testing may not predict clinical responses to indinavir," $1^{st}$ *International Workshop HIV Drug Resistance and Treatment Strategies and Eradication*, 1997; Abstract 47: 48-49.

Condra, Jon H.; "Resisting Resistance: Maximizing the Durability of antiretroviral Therapy," *Annals of Internal Medicine*, 1998; 128(11):951-955.

De Bethune et al.; "Does Natural or Acquired Resistance to Reverse Transcriptase and Protease Inhibitors, Observed in HIV-1 Groups M (Subtypes A-H) and O, Differ from Subtype B," $3^{rd}$ *International Workshop on HIV Drug Resistance and Treatment Strategies*, 1999; Abstract 49, 4(1).

De Oliveira, T. et al.; "Variability at Human Immunodeficiency Virus Type 1 Subtype C Protease Cleavage Sites: an Indication of Viral Fitness?," *Journal of Virology*, 2003; 77(17): 9422-9430.

Deeks et al.; "Novel Four-Drug Salvage Treatment Regimens After Failure of a Human Immunodeficiency Virus Type 1 Protease Inhibitor-Containing Regimen: Antiviral Activity and Correlation of Baseline Phenotypic Drug Susceptibility with Virologic Outcome," *The Journal of Infectious Disease*, 1999; 179:1375-1381.

DeScamps et al.; "Susceptibility of Human Immunodeficiency Virus Type 1 Group O Isolates to Antiretroviral Agents: In Vitro Phenotypic and Genotypic Analyses," *Journal of Virology*, 1997; 8893-8898.

Edelstein et al.; "Oligonucleotide Ligation Assay for Detecting Mutations in the Human Immunodeficiency Virus Type 1 *pol* Gene That are Associated with Resistance to Zidovudine, Didanosine, and Lamivudine," *Journal of Clinical Microbiology*, 1998; 569-572.

Eshleman et al.; "HIV1 isolate 420111k042398 from USA pol protein (pol) gene," downloaded from <http://www.ncbi.nlm.nih.gov/nuccore/AF357746> 2002: 1-2.

Esté et al.; "HIV Phenotype & Genotype Data Highlights," $2^{nd}$ *International Workshop on HIV Drug Resistance and Treatment Strategies*, Lake Maggiore, Italy, 1998.

Gianotti et al.; "Study on Mutations and Antiretroviral Therapy (SMART): Preliminary Results," *Antiviral Therapy*, 1999; 4(3):65-69.

Gianotti et al.; "The Rationale for a Study on HIV-1 Reverse Transcriptase Mutations and Outcome of Antiretroviral Therapy with Two Nucleoside Analogs," *Journal of Biological Regulators and Homeostatic Agents*, 1999; 158-162.

Gingeras et al.; "Use of Self-Sustained Sequence Replication Amplification Reaction to Analyze and Detect Mutations in Zidovudine-Resistant Human Immunodeficiency Virus," *The Journal of Infectious Diseases*, 1991; 164:1066-1074.

Gonzales et al.; "pol polyprotein (HIV-1)," downloaded from <http://www.ncbi.nlm.nih.gov/protein/AAK35843 2001>: 1-3.

Gunthard et al.; "Human Immunodeficiency Virus Replication and Genotypic Resistance in Blood and Lymph Nodes After a Year of Potent Antiretroviral Therapy," *Journal of Virology*, 1998; 2422-2428.

Hammer et al.; "Relationship of Phenotypic and Genotypic Resistance Profiles to Virological Outcome in a Trial of Abacavir, Nelfinavir, Efavirenz and Adefovir Dipivoxil in Patients with Virological Failure Receiving Indinavir," $3^{rd}$ *International Workshop on HIV Drug Resistance and Treatment Strategies*, 1999; 4(1); Abstract 64.

Harrigan et al.; "Drug Resistance and Short Term Virological Response in Patients Prescribed Multidrug Rescue Therapy," $3^{rd}$ *International Workshop on HIV Drug Resistance and Treatment Strategies*, 1999; 4(1); Abstract 62.

Hertogs et al.; "The RT-Antivirogram™: a rapid and accurate method to determine phenotypic (multi)-drug resistance in plasma of patients treated with various HIV-1 RT inhibitors," $5^{th}$ *International Workshop on HIV Drug Resistance*, 1996; Whistler, Canada, Abstract 64.

Hertogs et al.; "A Blinded Comparative Analysis of Two Genotyping Service Laboratories: Full Sequence Analysis of HIV-1 Protease and Reverse Transcriptase," $3^{rd}$ *International Workshop on HIV Drug Resistance and Treatment Strategies*, 1999; 4(1); Abstract 87.

Hertogs et al.; "Common, Rare and New Genotypic and/or Phenotypic HIV-1 Resistance Profiles Observed in Routine Clinical Practice: A Survey of Over 5000 Isolates," $3^{rd}$ *International Workshop on HIV Drug Resistance and Treatment Strategies*, 1999; 4(1); Abstract 108.

Hertogs et al.; "Performance characteristics of phenotypic drug resistance testing (Antivirogram) in monitoring of anti-HIV therapy, "*International Workshop on HIV Drug Resistance, Treatment Strategies and Eradication*, 1997; St. Petersburg, Florida; Abstract 43.

Hertogs et al.; "Testing for HIV-1 Drug Resistance: New Developments and Clinical Implications," *Recent Res. Dev. Antimicrob. Agents Chemother.*, 1999; 3(Pt. 1):83-104.

Hirsch et al.; "Antiretroviral Drug Resistance Testing in Adults with HIV Infection," *JAMA*, 1998; 279(24):1984-1991.

HIV Database, http://hiv-web.lanl.gov/content/index.

Holodniy et al.; "Human Immunodeficiency Virus Reverse Transcriptase Codon 215 Mutations Diminish Virologic Response to Didanosine-Zidovudine Therapy in Subjects with Non-Syncytium-Inducing Phenotype," *The Journal of Infectious Diseases*, 1996; 174:854-857.

Hsu et al.; "Higher Fidelity of RNA-Dependent DNA Mispair Extension by M184V Drug-Resistant than Wild-type Reverse Transcriptase of Human Immunodeficiency Virus Type 1," *Nucleic Acids Research*, 1997; 25(22):4532-4536.

Ives et al.; "Emergence of Resistant Variants of HIV in vitro During Monotherapy with the Proteinase Inhibitor Saquinavir," *Journal of Antimicrobial Chemotherapy*, 1997; 39:771-779.

Kaufmann, G. R. et al.; "Impact of HIV Type 1 protease, Reverse Transcriptase, Cleavage Site, and p6 Mutations on the Virological Response to Quadruple Therapy with Saquinavir, Ritonavir, and Two Nucleoside Analogs," *AIDS Research and Human Retroviruses*, 2001; 17(6):487-497.

Kellam et al.; "Fifth Mutation in Human Immunodeficiency Virus Type 1 Reverse Transcriptase Contributes to the Development of High-Level Resistance to Zidovudine," *Proc. Natl. Acad. Sci. USA*; 1992; 89:1934-1938.

Kemp et al.; "A Novel Polymorphism at Codon 333 of Human Immunodeficiency Virus Type 1 Reverse Transcriptase Can Facilitate Dual Resistance to Zidovudine and L-2', 3'-Dideoxy-3'-Thiacytidine," *Journal of Virology*, 1998; 72:5093-5098.

Kempf et al.; "Analysis of Virological Response to ABT-378/ Ritonavir Therapy in Protease Inhibitor-Experienced Patients with Respect to Baseline Viral Phenotype and Genotype," $3^{rd}$ *International Workshop on HIV Drug Resistance and Treatment Strategies*, 1999; 4(1); Abstract 8.

Kuritzkes, Daniel R.; "HIV Resistance to Current Therapies," *Antiviral Therapy*, 1997; 2(3);61-67.

Larder et al.; "A Family of Insertion Mutations Between Codons 67 and 70 of Human Immunodeficiency Virus Type 1 Reverse Transcriptase Confer Multinucleoside Analog Resistance," *Antimicrob. Agents Chemother.*, 1999; 43(8):1961-1967.

Larder et al.; "HIV with Reduced Sensitivity to Zidovudine (AZT) Isolated During Prolonged Therapy," *Reports*, 1989; 243:1731-1734.

Larder et al.; "Multi-nucleoside drug resistance is conferred by a family of insertion mutations in HIV-1 reverse transcriptase," *Interscience Conference on Antimicrobial Agents and Chemotherapies*, 1998; 38:28 (Abstract No. LB-4).

Larder et al.; "Predicting HIV-1 Phenotypic Resistance from Genotype Using a Large Phenotype-Genotype Relational Database," *3rd International Workshop on HIV Drug Resistance and Treatment Strategies*, 1999; 4(1); Abstract 59.

Larder et al.; "Tipranavir Inhibits Broadly Protease Inhibitor-Resistant HIV-1 Clinical Samples," *AIDS*, 2000; 14:1943-1948.

Larder et al.; "Tipranavir is Active Against a Large Selection of Highly Protease Inhibitor-Resistance HIV-1 Clinical Samples," *3rd International Workshop on HIV Drug Resistance and Treatment Strategies*, 1999; 4(1); Abstract 5.

Leigh-Brown et al.; "Associations Between Amino Acids in the Evolution of HIV Type 1 Protease Sequences Under Indinavir Therapy," *AIDS Research and Human Retroviruses*, 1999; 15(3):247-253.

Lennerstrand et al.; "Mechanism of Zidovudine and Stavudine Resistance for HIV-1 RT with Amino Acid Insertions Between Codons 68 and 70," *3rd International Workshop on HIV Drug Resistance and Treatment Strategies*, 1999; 4(1); Abstract 32.

Leriche-Guerin et al.; "Correlation Between Antiretroviral Resistance Mutations, Biological Parameters, and Clinical Evolution in Zidovudine-Treated Patients Infected with Human Immunodeficiency Virus Type 1," *Eur. J. Clin. Microbiol. Infect. Dis.*, 1997; 16:660-668.

Lorenzi et al.; "Impact of Drug Resistance Mutations on Virologic Response to Salvage Therapy," *AIDS*, 1999; 13:F17-F21.

Martinez et al.; "protease (HIV-1)," downloaded from <http://www.ncbi.nlm.nih.gov/protein/AAF29689> 2000.

Miller et al.; "Correlates of Resistance to Individual Nucleoside Drugs in Patients Who Have Never Taken Them," *3rd International Workshop on HIV Drug Resistance and Treatment Strategies*, 1999; 4(1); Abstract 41.

Miller et al.; "Phenotypic Susceptibility to Adefovir Dipivoxil in Clinical Samples with Defined RT Genotypic Resistance Patterns," *3rd International Workshop on HIV Drug Resistance and Treatment Strategies*, 1999; 4(1); Abstract 40.

Miller et al.; "Prevalence of Baseline Drug Resistance Mutations in Primary HIV Infection Patients from the QUEST Study," *3rd International Workshop on HIV Drug Resistance and Treatment Strategies*, 1999; 4(1); Abstract 141.

Mohamed et al.; "The Sequential Occurrence of *pol* 215 and *pol* 41 Zidovudine Resistance Mutations is Associated in an Additive Fashion with Low CD4 Cell Counts and High Plasma and Cellular HIV Viral Load," *Antiviral Research*, 1998; 39:47-53.

Moyle, G.; "Current Knowledge of HIV-1 Reverse Transcriptase Mutations Selected During Nucleoside Analogue Therapy: The Potential to Use Resistance Data to Guide Clinical Decisions," *Journal of Antimicrobial Chemotherapy*, 1997; 40:765-777.

Moyle, G.; "Viral Resistance Patterns Selected by Antiretroviral Drugs and Their Potential to Guide Treatment Choice," *Exp. Opin. Invest. Drugs*, 1997; 6(8):943-964.

Nakano et al.; "Clonal Selection of HIV Type 1 Variants Associated with Resistance to Foscarnet in Vitro: Confirmation by Molecular Evolutionary Analysis," *Aids Research and Human Retroviruses*, 1997; 13(7):563-573.

International Search Report dated Jan. 4, 2005 for PCT/EP03/050280.

International Search Report dated Nov. 10, 2003, for PCT/EP03/50277.

International Search Reported dated Oct. 22, 2003 for PCT/EP03/50279.

Perez-Olmeda et al.; "Usefulness of Genotypic Analysis of Resistance to Nucleoside Analogues in the Clinical Setting," *Eur. J. Clin. Microbrial Infect. Dis.*, 1999; 18:448-449.

Piketty et al..; "Efficacy of a Five-Drug Combination Including Ritonavir, Saquinavir and Efavirenz in Patients Who Failed on a Conventional Triple-Drug Regimen: Phenotypic Resistance to Protease Inhibitors Predicts Outcome of Therapy," *AIDS*, 1999; 13:F71-F77.

Ren et al.; "Crystal Structures of HIV-1 RT Inhibitor Complexes: 'Second Generation' NNRTIs, Efavirenz and S-1153 (AG1549), and NNRTI- and NRTI-resistant Mutant Forms," *3rd International Workshop on HIV Drug Resistance and Treatment Strategies*, 1999; 4(1); Abstract 20.

Saag et al.; "A Short-Term Clinical Evaluation of L-697,661, a Non-Nucleoside Inhibitor of HIV-1 Reverse Transcriptase," *The New England Journal of Medicine*; 1993; 329:1065-1072.

Schapiro et al.; "Clinical Cross-Resistance Between the HIV-1 Protease Inhibitors Saquinavir and Indinavir and Correlations with Genotypic Mutations," *AIDS*, 1999; 13:359-365.

Schinazi et al.; "Mutations in Retroviral Genes Associated with Drug Resistance," *International Antiviral News*, 1997; 5:129-142.

Schinazi et al., "Mutations in Retroviral Genes Associated with Drug Resistance: 2000-2001 Update," *International Antiviral News*, 2000; 8(5):65-91.

Schmidt et al.; "HIV-1 isolate 992286 from Germany pol protein (pol) gene," downloaded from <http://www.ncbi.nlm.nih.gov/nucleotide/AF347471>, 2002: 1-2.

Schmidt et al.; "pol protein (HIV-1)," downloaded from <http://www.ncbi.nlm.nih.gov/protein/AAK32676>, 2002: 1-2.

Schmidt et al.; "Simple Algorithm Derived from a Geno-/Phenotypic Database to Predict HIV-1 Protease Inhibitor Resistance," *AIDS*, 2000; 14:1731-1738.

Schmit et al.; "Recent Advances in Antiretroviral Therapy and HIV Infection Monitoring"; *Intervirology*, 1997; 40:304-321.

Schmit et al.; "Resistance-related Mutations in the HIV-1 Protease Gene of Patients Treated in 1 Year with the Protease Inhibitor Ritonavir (ABT-538)," *AIDS*, 1996; 10:995-999.

Seki et al.; "Isolation and characterization of human immunodeficiency virus type-1 mutants resistant to the non-nucleotide reverse transcriptase inhibitor MKC-442," *Antiviral Chemistry & Chemotherapy*, 1995; 6(2):73-79.

Servais et al.; "Comparison of DNA Sequencing and a Line Probe Assay for Detection of Human Immunodeficiency Virus Type 1 Drug Resistance Mutations in Patients Failing Highly Active Antiretroviral Therapy," *Journal of Clinical Microbiology*, 2001; 39(2):454-459.

Servais, J.A.; "V-1 Reverse Transcriptase (human immunodeficiency virus 1), Accession No. CAB86592," downloaded from http://www/ncbi.nlm.nih.gov/entrez/viewer.fcgi?db=protein&val=7529531, 2006.

Shafer et al.; "HIV-1 isolate PCCPROT48 from USA, protease (pol) gene," downloaded from <http://www.ncbi.nlm.nih.gov/nucleotide/AF085133>, 2001.

Shafer et al.; "Human Immunodeficiency Virus Reverse Transcriptase and Protease Sequence Database," *Nucleic Acids Research*, 1999; 22(1):348-352.

Shafer et al.; "Human Immunodeficiency Virus Reverse Transcriptase and Protease Sequence Database," *Nucleic Acids Research*, 2000; 28(1):346-348.

Tamalet et al.; "Multidrug Resistance Genotypes (Insertions in the β3-β4 Finger Subdomain and MDR Mutations) of HIV-1 Reverse Transcriptase from Extensively Treated Patients: Incidence and Association with Other Resistance Mutations," *Virology*, 2000; 270:310-316.

Vandamme et al.; "Managing Resistance to Anti-HIV Drugs," *Drugs*, 1999; 337-361.

Vella, S.; "Advances in the Virology of HIV Infection and Implications for Clinical Management," *Aids Clinical Care*, 1998; 10(3):17-19.

Verbiest et al.; "An Epidemiological Prospective Survey Assessing the Prevalence of HIV-1 Drug Resistance in 230 HIV-1-Positive Antiretroviral-Naïve Patients from the USA," *3rd International Workshop on HIV Drug Resistance and Treatment Strategies*, 1999; 4(1); Abstract 122.

Vergne et al., "POL precursor" downloaded from http://www.ncbi.nlm.nih.gov/protein/CAC03089, 2000: 1-2.

Verheyen, J. et al.; "Compensatory mutations at the HIV cleavage sites p7/p1 and p1/p6-gag in therapy -naive and therapy-experienced patients," *Antiviral Therapy*, 2006; 11(7): 879-887.

Villahermosa et al.; "Evaluation of Mixtures of Wild-Type HIV-1 and HIV-1 with Resistance Point Mutations Against Reverse Transcriptase Inhibitors," *Antiviral Therapy*, 1998; 3:221-227.

Vingerhoets et al.; "The Accuracy and Reproducibility of High Throughput Genotypic and Phenotypic HIV-1 Resistance Testing Under EN45001 and CLIA Accreditation Labels," *3rd International Workshop on HIV Drug Resistance and Treatment Strategies*, 1999; 4(1); Abstract 77.

Walter et al.; "Rapid, Phenotypic HIV-1 Drug Sensitivity Assay for Protease and Reverse Transcriptase Inhibitors," *Journal of Clinical Virology*, 1999; 13:71-80.

Watkins et al.; "Protease HIV1," downloaded from http://www.ncbi.nlm.nih.gov/protein/Q7ZCQ9, 2000.

Watkins et al.; "Selection of High-Level Resistance to Human Immunodeficiency Virus Type 1 Protease Inhibitors," *Antimicrobial Agents and Chemotherapy*, 2003; 47(2):759-769.

Weber et al.; "Molecular Mechanics Analysis of Drug-Resistant Mutants of HIV Protease," *Protein Engineering*, 1999; 12(6):469-474.

Wegner et al.; "High Frequency of Antiretroviral Drug Resistance in HIV-1 From Recently Infected Therapy-Naïve Individuals," *3rd International Workshop on HIV Drug Resistance and Treatment Strategies*, 1999; 4(1); Abstract 119.

Wegner et al.; "Prevalence of Genotypic and Phenotypic Resistance to Anti-Retroviral Drugs in a Cohort of Therapy-Naïve HIV-1 Infected US Military Personnel," *AIDS*, 2000; 14:1009-1015.

Wegner et al.; "The Potential Role of Resistance Testing and Therapeutic Drug Monitoring in the Optimization of Antiretroviral Drug Therapy," *3rd International Workshop on HIV Drug Resistance and Treatment Strategies*, 1999; 4(1); Abstract 112.

Winters et al.; "Human Immunodeficiency Virus Type 1 Reverse Transcriptase Genotype and Drug Susceptibility Changes in Infected Individuals Receiving Dideoxyinosine Monotherapy for 1 to 2 Years," *Antimicrobial Agents and Chemotherapy*, 1997; 41(4):757-762.

Yahi et al.; "Mutation Patterns of the Reverse Transcriptase and Protease Genes in Human Immunodeficiency Virus Type 1-Infected Patients Undergoing Combination Therapy: Survey of 787 Sequences," *Journal of Clinical Microbiology*, 1999; 37(12):4099-4106.

Yee et al.; "Prospects for Gene Therapy Using HIV-Based Vectors," *Somatic Cell and Molecular Genetics*, 2001; 26(1-6):159-174.

Yin et al.; "Overcoming HIV drug resistance through rational drug design based on molecular, biochemical, and structural profiles of HIV resistance," *Cellular Molecular Life Sciences*, 2006, 63:1706-1724.

Zhang Y-M, et al.; "Drug Resistance during Indinavir Therapy Is Caused by Mutations in the Protease Gene and in Its Gag Substrate Cleavage Sites," *Journal of Virology*, 1997; 71(9): 6662-6670.

Zolopa et al.; "A Comparison of Phenotypic, Genotypic and Clinical/Treatment History Predictors of Virological Response to Saquinavir/Ritonavir Salvage Therapy in a Clinic-based Cohort," *3rd International Workshop on HIV Drug Resistance and Treatment Strategies*, 1999; 4(1); Abstract 68.

Zolopa et al.; "HIV-1 Genotypic Resistance Patterns Predict Response to Saquinavir-Ritonavir Therapy in Patients in whom Previous Protease Inhibitor Therapy Had Failed," *Annals of Internal Medicine*, 1999; 131(11): 813-821.

"Guidance for Industry," U.S. Department of Health and Human Services, Food and Drug Administration, http://www.fda.gpv/cder/guidance/index.htm, 1990.

Abstract: International Congress on Drug Therapy in HIV Infection, 1998; 12(4); AIDSonline.com.

Hertogs et al.; "Comprehensive HIV Drug Resistance Monitoring Using Rapid, High-Throughput Phenotypic and Genotypic Assays with Correlative Data Analysis," *International Congress on Drug Therapy in HIV Infections*, 1998; 12(4):S11 (OP3.4).

International Search Report dated Apr. 12, 2008, for PCT/EP08/056356.

International Search Report dated Jul. 17, 2003, for PCT/EP01/012338.

International Search Report dated Nov. 10, 2003 for PCT/EP03/50277.

Larder et al.; "A Complete Survey in Over 1,500 Clinical HIV-1 Isolates, of Phenotypic and Genotypic Protease Inhibitor Resistance Profiles (Including Gag Cleavage Site Sequences) and Their Relation to Therapy History," *International Congress on Drug Therapy in HIV Infections*, 1998; 12(4):S11 *Abstract Poster*, OP3.5.

Matayoshi et al.; "Novel Flurogenic Substrates for Assaying Retroviral Proteases by Resonance Energy Transfer," *Science*, 1990; 247:954-958.

Wang et al.; "Design and Synthesis of New Fluorogenic HIV Protease Substrates Based on Resonance Energy Transfer," *Tetrahedron Letters*, 1990: 6493-6496.

\* cited by examiner

MUTATIONAL PROFILES IN HIV-1 PROTEASE CORRELATED WITH PHENOTYPIC DRUG RESISTANCE

CROSS REFERENCE TO RELATED APPLICATIONS

This application is a divisional of U.S. application Ser. No. 10/518,525, filed Dec. 22, 2004, now U.S. Pat. No. 7,473,524, which is a U.S. National Phase Application of International Application No. PCT/EP2003/050280, filed Jun. 30, 2003, which claims priority from U.S. Provisional Application No. 60/393,005, filed Jul. 1, 2002. The complete disclosures of the aforementioned related applications are hereby incorporated herein by reference for all purposes.

The present invention is directed to the field of nucleic acid diagnostics and the identification of base variation in target nucleic acid sequences. The invention provides novel mutations or mutational profiles of HIV-1 reverse transcriptase gene correlated with a phenotype causing alterations in sensitivity to anti-HIV drugs. The present invention also relates to the use of genotypic characterization of a target population of HIV and the subsequent association, i.e. correlation, of this information to phenotypic interpretation in order to correlate virus mutational profiles with drug resistance. The invention further relates to methods of utilizing the mutational profiles of the invention in databases, drug development, i.e., drug design, and drug modification, therapy and treatment design and clinical management.

The development and standardization of plasma HIV-1 RNA quantification assays has led to the use of viral load measurements as a key therapy response monitoring tool. The goal of antiretroviral therapy is to reduce plasma viremia to below the limit of detection on a long-term basis. However, in a significant number of patients, maximal suppression of virus replication is not achieved and for those in whom this goal is reached, a significant number experience viral load rebound. Viral load data provide no information on the cause of the failure.

Therapy failure may be due to a number of factors, including insufficient antiviral activity of the regimen, individual variations in drug metabolism and pharmacodynamics, difficulties in adhering to dosing regimen, requirements for treatment interruption due to toxicity, and viral drug resistance. Moreover, drug resistance may develop in a patient treated with sub-optimal antiretroviral therapy or a patient may be infected with drug-resistant HIV-1. Although drug resistance may not be the primary reason for therapy failure, in many cases any situation which permits viral replication in the presence of an inhibitor sets the stage for selection of resistant variants. Viral drug resistance can be defined as any change in the virus that improves replication in the presence of an inhibitor. HIV-1 drug resistance was first described in 1989 and involved patients that had been treated with zidovudine monotherapy (Larder, B. A., et al., Science 243, 1731-1734 (1989)). Emergence of resistance is almost always being observed during the course of treatment of patients with single antiretroviral drugs. Similarly, in vitro passage of viral cultures through several rounds of replication in the presence of antiretroviral compounds leads to the selection of viruses whose replication cycle is no longer susceptible to the antiretroviral compounds used. Resistance development has also been observed with the introduction of dual nucleoside reverse transcriptase inhibitors (NRTI) combination therapy as well as during the administering of the more potent non-nucleoside reverse transcriptase inhibitors (NNRTIs), protease inhibitors (PIs) and combinations thereof. Individual antiretroviral agents differ in the rate at which resistance develops: selection for resistant variants may occur within weeks of treatment or resistance may emerge after a longer treatment period.

Extensive genetic analysis of resistant viral isolates generated through in vivo or in vitro selection has revealed that resistance is generally caused by mutations at some specific site(s) of the viral genome. The mutational patterns that have been observed and reported for HIV-1 and that are correlated with drug resistance are very diverse: some antiretroviral agents require only one single genetic change, while others require multiple mutations for resistance to appear. A summary of mutations in the HIV genome correlated with drug resistance has been compiled (See e.g. Schinazi, Int. Antiviral News. 6, 65 (2000)). Electronic listings with mutations are available at different web locations such as hiv-web.lanl.gov/content/index, www.hivb.stanford.edu, and www.hivresistanceweb.com.

A genetic mutation is normally written in reference to the wild type virus, i.e., K101N refers to replacement of a Lysine at codon 101 with a Asparagine (The Molecular biology of the Cell, 1994, Garland Publishing, NY). However, the mutations of the invention do not depend on the wild-type example listed in order to be within the practice of the invention. For example, the mutation 101N, refers to an Asparagine at the 101 codon regardless of the whether there was a Lysine at 101 prior to mutation. Alternatively, it may be said that a particular amino acid occurs at a given position, wherein "position" is equivalent to "codon". Mutations can also be identified in nucleic acids such as RNA, DNA, mRNA.

The degree of susceptibility of a genetic variant to an antiretroviral compound is expressed herein relative to the wild-type virus (HIV IIIB/LAI reference sequence) as found, for example, in GenBank, the sequence of which is hereby incorporated by reference (K03455, gi 327742, M38432). An alteration in viral drug sensitivity is defined as a change in resistance or a change in susceptibility of a viral strain to said drug. Susceptibilities are generally expressed as ratios of $EC_{50}$ or $EC_{90}$ values (the $EC_{50}$ or $EC_{90}$ value being the drug concentration at which 50% or 90% respectively of the viral population is inhibited from replicating) of a viral strain under investigation compared to the wild type strain. Hence, the susceptibility of a viral strain can be expressed as a fold change in susceptibility, wherein the fold change is derived from the ratio of for instance the $EC_{50}$ values of a mutant viral strain compared to the wild type. In particular, the susceptibility of a viral strain or population may also be expressed as resistance of a viral strain, wherein the result is indicated as a fold increase in $EC_{50}$ as compared to wild type $EC_{50}$.

As antiretroviral drugs are administered for longer periods, mostly in combination with each other, and as new antiretrovirals are being developed and added to the present drugs, new resistance-correlated genetic variants are being identified. Of particular importance is that the combination of antiretroviral agents can influence resistance characteristics.

Once viral resistance has developed, salvage therapy options may be severely restricted due to cross-resistance within each drug class. This is as important for initial treatment as for when a therapy change is called for in order to minimize the emergence of resistance and improve the long-term prognosis of the patient. The choice of therapy regimen will be supported by knowledge of the resistance profile of the circulating virus population. Additionally, therapy combinations will have a greater chance of being effective if they include agents that have a demonstrated potential of suppressing a particular virus population.

A number of applications describe the occurrence of mutations in HIV and their correlation to the development of drug resistance (WO 00/73511; WO 02/33402; WO 02/22076; WO 00/78996). The instant invention adds to the art mutations in the reverse transcriptase gene and their correlation i.e. association to viral drug resistance.

DETAILED DESCRIPTION OF THE INVENTION

The knowledge that the mutation 386A correlates with a fold change in resistance can be applied in certain useful methods. The present invention relates to methods for evaluating the effectiveness of a reverse transcriptase inhibitor, based on the presence of at least one mutation 386A in HIV reverse transcriptase. The presence of said mutation correlates to a fold change in susceptibility or resistance of an HIV viral strain towards at least one reverse transcriptase drug. The effectiveness of a reverse transcriptase inhibitor in the presence of at least one of said mutations may be determined using e.g. enzymatic, phenotypic and genotypic methods. The correlation between the mutational profiles in HIV reverse transcriptase and drug usage may be useful for clinical toxicological and forensic applications. A combined approach involving genotypic and phenotypic resistance testing to correlate mutations with resistance phenotypes may be used. More in particular, the present invention provides a correlation between at least one strain of HIV having at least one 386A mutation in HIV reverse transcriptase and a fold change in resistance.

The effectiveness of a reverse transcriptase inhibitor as an antiviral therapy for a patient infected with at least one HIV strain comprising mutant reverse trascriptase may be determined using a method comprising: (i) collecting a sample from an HIV-infected patient; (ii) determining whether the sample comprises a HIV reverse transcriptase having at least one mutation 386A; and (iii) correlating the presence of said at least one mutation of step (ii) to a change in effectiveness of said reverse transcriptase inhibitor In general a change in effectiveness can be expressed as a fold change in resistance. The fold change may be determined using a cellular assay including the cytopathogenic assay or the Antivirogram® (WO 97/27480). Alternatively, the fold change in susceptibility may be derived from database analysis such as the VirtualPhenotype™ (WO 01/79540). A decrease in susceptibility vis-à-vis the wild type virus correlates to an increased viral drug resistance, and hence reduced effectiveness of said drug. To determine the viral drug susceptibility the activity of the mutant enzyme may be compared to the activity of a wild type enzyme. In phenotyping assays pseudotyped viruses may be used. The mutations present in HIV reverse transcriptase may be determined at the nucleic acid or amino acid level using sequencing or hybridization techniques. A report may be generated that shows the region of the patient virus that has been sequenced, including at least one mutation 386A. The report may include antiretroviral drugs, drug(s) for which a known resistance-associated mutation has been identified and/or to what extent the observed mutation(s) selected from at least 386A are indicative of resistance to drugs. The sample to be evaluated can be a bodily fluid including blood, serum, plasma, saliva, urine, or a tissue including gut tissues.

The fact that particular data correlate, indicates that a causal relationship exits between the data. Hence, a particular result renders a particular conclusion more likely than other conclusions.

A drug effective against mutant HIV reverse transcriptase may be identified by a method, comprising: (i) providing a nucleic acid comprising HIV reverse transcriptase comprising at least one mutation 386A; (ii) determining a phenotypic response to said drug for said HIV recombinant virus; and (iii) identifying a drug effective against mutant HIV based on the phenotypic response of step (ii). The nucleic acid comprising HIV of step (i) may be recombined into a proviral nucleic acid deleted for said sequence to generate a recombinant HIV virus.

Identifying a drug is defined as making a selection of drugs clinically available based on the effectiveness of said drug. In addition to the selection of clinically available drugs identifying also relates to the selection of clinical drug candidates. The phenotypic response may be determined using cellular assays such as the Antivirogram®. An effective drug against mutant HIV comprising at least one mutation 386A in reverse transcriptase is defined as a drug having a phenotypic response expressed, as e.g. a fold change in susceptibility lower than a defined cut-off that may be determined for a drug.

An other useful method for identifying, a drug effective against mutant HIV reverse transcriptase comprises: (i) providing a HIV reverse transcriptase comprising at least one mutation 386A, (ii) determining the activity of said drug on said HIV reverse transcriptase; (iii) determining the activity of said drug on wild type HIV reverse transcriptase; (iv) determining the ratio of the activity determined in step (iii) over the activity determined in step (ii); (v) identifying an effective drug against mutant HIV based on the ratio of step (iv). A ratio lower than a defined cut-off value that can be specific for said drug is indicative that the drug is effective against mutant HIV (WO 02/33402).

The activity of said drug on mutant HIV reverse transcriptase having at least one mutation 386A, can be determined in an enzymatic assay, wherein the mutant reverse transcriptase, is compared to the wild type enzyme by its enzymatic characteristics (e.g. Maximal velocity ($V_{max}$), Michaelis-Menten constant ($K_m$), catalytic constant ($k_{cat}$)) (Antimicrob. Agents Chemotherap. 1989 33(12), 2109-2114; Antimicrob. Agents Chemotherap. 1989 33(10), 1729-1734; Anal Biochem. 1996, 235(2) 141-152). An activity means any output generated by the assay including fluorescence, fluorescence polarization, luminiscence, absorbance, radioactivity, resonance energy transfer mechanisms, magnetism.

The response of a mutant HIV reverse transcriptase having at least one mutation 386A may be expressed as viral fitness (WO 00/78994). This viral fitness can be defined as the ability of a viral strain to replicate in the presence or absence of a component, such as a reverse transcriptase inhibitor. This viral fitness is dependent on a combination of factors including viral factors which include mutations occurring in viral proteins, host factors which include immune responses, differential expression of membrane proteins and selective pressures which include the presence of antiviral agents such as reverse transcriptase inhibitors.

Interestingly, the reverse transcriptase inhibitors that can be used in the present methods include Zidovudine, Nevirapine, Efavirenz, Abacavir, Capravirine, Lamivudine, Didanosine, Stavudine, Adefovir, Zalcitabine, Delavirdine, DPC-086, DPC-083, Tenofovir, and compound 1 (Benzonitrile, 4-[[6-amino-5-bromo-2-[(4-cyanophenyl)amino]-4-pyrimidinyl]oxy]-3,5-dimethyl-, compound 1). In particular, the reverse transcriptase inhibitor is selected from Nevirapine, Efavirenz, Capravirine, DPC-086 and compound 1. Suitably, the inhibitor is selected from compound 1, Nevirapine and Efavirenz.

Conveniently, the methods of the present invention are performed using samples of an HIV-infected patient that has been treated with at least a reverse transcriptase inhibitor. More in particular, the patient contains mutant viruses bearing at least one additional mutation at position in the HIV reverse transcriptase selected from 41, 62, 65, 67, 69, 70, 74, 75, 98, 100, 101, 103, 106, 108, 116, 118, 138, 151, 178, 181, 184, 188, 190, 210, 215, 219, 225, 227, 230, 234, 236, 238, and 318. Even more in particular, the mutant viruses are resistant towards the therapy the patient is taken.

A vector comprising an HIV sequence having at least one mutation 386A in the HIV reverse transcriptase gene may be useful for the phenotypic analysis. The present knowledge about the correlation between a fold change in susceptibility and the presence of at least one mutation 386A in HIV reverse transcriptase can be used to prepare an isolated and purified HIV reverse transcriptase sequence having at least one mutation 386A.

The knowledge of the mutations of the present invention offers the possibility to develop probes and primers directed to said mutations. An isolated and purified oligonucleotide comprising a HIV reverse transcriptase sequence of 5 to 100 bases comprising at least one mutation 386A, may be useful for in vitro diagnosis of viral drug resistance. Suitable oligonucleotides for nucleic acid amplifying technologies contain 5 to 35 nucleic acid bases. More suitably such oligonucleotide contains between 15 to 30 nucleic acid bases. An oligonucleotide may contain the mutant base at the 3' end so as to enable the detection of the mutant using PCR. Oligonucleotides may also be used as probes including molecular beacons (Tyagi, Nature Biotechnol 1998, 16(1) 49-53), and TaqMan probes.

A computer system comprising at least one database correlating the presence of at least one mutation in a human immunodeficiency virus reverse transcriptase and fold change in susceptibility of at least one strain of HIV to a reverse transcriptase inhibitor, comprising at least one record corresponding to a correlation between at least one mutation 386A, and treatment with at least a reverse transcriptase inhibitor can be used for evaluating resistance towards therapy.

A neural network that predicts the development of therapeutic agent resistance or sensitivity against at least one viral strain comprising at least one mutation 386A can be used (WO 01/95230).

Genotyping Methodologies

Resistance of HIV to antiretroviral drugs may be determined at the genotypic level by identifying mutations in the HIV-1 genome and by inferring the resistance of HIV-1 to antiretroviral drugs through searching for mutational patterns known to correlate with resistance. Assays for detection of mutations in HIV-1 may be based on polymerase chain reaction (PCR) amplification of viral genomic sequences. These amplified sequences are then analyzed using either hybridization or sequencing techniques. Hybridization-based assays include primer-specific PCR, which makes use of synthetic oligonucleotides designed to allow selective priming of DNA synthesis. See Larder, B. A., et al., AIDS 5, 137-144 (1991); Richman, D. D., et al., J. Infect. Dis. 164, 1075-1081 (1991); Gingeras, T. R., et al., J. Infect. Dis. 164, 1066-1074 (1991). Only when primer sequences match the target sequence (wild-type or mutant) at the 3' end, is amplification of target sequences possible and DNA fragments are produced. Knowledge of the primer sequences allows one to infer the sequence of the viral isolate under investigation, but only for the region covered by the primer sequences. Other hybridization-based assays include differential hybridization (Eastman, P. S., et al., J. Acq. 1 mm. Def. Syndr. Human Retrovirol. 9, 264-273 (1995); Holodniy, M., et al., J. Virol. 69, 3510-3516 (1995); Eastman, P. S., et al., J. Clin. Micro. 33, 2777-2780 (1995).); Line Probe Assay (LiPAJ HIV-11 RT, Innogenetics) (Stuyver, L., et al., Antimicrob. Agents Chemotherap. 41, 284-291 (1997)); and biochip technology such as GENECHIP® technology (Affymetrix) (D'Aquila, R. T. Clin. Diagnost. Virol. 3, 299-316 (1995); Fodor, S. P. A. et al., Nature 364, 555-556 (1993); Fodor, S. P. A. Science 227, 393-395 (1997). The sequence may also be determined using mass spectroscopic technologies. DNA sequencing assays provide information on all nucleotides of the sequenced region. Sequencing results may be reported as amino acid changes at positions in the protease gene and the reverse transcriptase gene compared to the wild-type reference sequence. The changes included in the genotyping report may be limited to mutations at positions known to manifest drug resistance-associated polymorphisms. Polymorphisms at positions not associated with drug resistance may be omitted.

Phenotyping Methodologies

Phenotyping assays measure the ability of a replicating virus to grow in the presence of compounds compared to a wild-type reference virus such as e.g. HIV-1/LAI, HIV-1/NL4.3, HIV-1/HXB2 or e.g. HIV-2/ROD. Alternatively, phenotyping assays are performed with pseudotyped viruses not able to replicate (WO 02/38792). Consequently, these assays directly measure the degree of viral susceptibility to specific inhibitors. In this case, one measures the effect of all mutational interactions, the effects of genetic changes as yet unknown or not previously identified, the effect of the background genotype, etc., on the phenotype. Some phenotypic assays are discussed below.

Cytopathic Effect Assay (CPE Assay)

Determination of the antiviral activity of a compound was done as described in Pauwels R. et al. (J Virol Methods 1988; 20(4):309-21). Various concentrations of the test compounds were brought into each well of a flat-bottom microtiter plate. Subsequently, HIV and MT4 cells were added to a final concentration of 200-250 50% cell culture infectious doses ($CCID_{50}$)/well and 30,000 cells/well, respectively. After 5 days of incubation (37° C., 5% $CO_2$), the cytopathic effect of the replicating virus was determined by the tetrazolium calorimetric MTT method. The dose protecting 50% of the cells from virus cytopathic effect was defined as the $EC_{50}$, while the dose achieving 90% protection was defined as the $EC_{90}$.

Reporter Gene Assay

The reporter gene assay used MT4-LTR-EGFP cells. Upon infection by HIV-1, the expression of the viral that product increases transcription from the HIV-1 LTR promoter, leading to high-level expression of the reporter gene product.

The assay procedure was similar to the CPE assay except for the end reading of the assay, which was performed on day 3 by measuring the relative fluorescence of treated cultures and comparing this with the relative fluorescence of untreated cultures. The $EC_{50}$ or the $EC_{90}$ of a compound was defined as the concentration that inhibited the relative fluorescence by 50% or 90% respectively.

Antiviral Assay with PBMC Cultures

The purification and activation of PBMCs as well as the antiviral assays were carried out as described (CDER. Guidance for Industry Points to Consider in the Preclinical Development of Antiviral Drugs. 1990). The assay measured the extent that a drug inhibits HIV p24 antigen production by peripheral blood mononuclear cells (PBMC) cultures acutely infected with a viral strain. The susceptibility determination uses phytohaemaglutinine (PHA)-stimulated PBMCs from normal donors. In the in vitro infection experiments 1000 $CCID_{50}$ per million PHA-stimulated PBMCs was used. Cultures were split ½ every 3 to 4 days and compound was added together with the addition of new medium.

The p24 antigen production was measured using a commercial kit, according to the manufacturer protocol (NEN), at the moment that the p24 production of untreated infected cultures is maximal; i.e. between 7 and 11 days after infection.

The % p24 production was calculated by means of following equation:

$$\%p24 = 100 \times \frac{[p24]Sample - [p24]Mock\_Control}{[p24]HIV\_Contrd - [p24]Mock\_Control}$$

where $[p24]_{Sample}$ is the p24 concentration in an infected treated culture, $[p24]_{HIV\_Control}$ is the p24 concentration in an infected untreated culture and $[p24]_{Mock\_Control}$ is the p24 concentration in a mock-infected culture. The dose achieving 50% p24 production according to the above formula was defined as the $EC_{50}$, while the dose achieving 10% p24 production according to the above formula was defined as the $EC_{90}$.

Antiviral Assay with Monocytes/Macrophages

The assay measured the extent that a drug inhibits HIV p24 antigen production by primary monocytes/macrophages acutely infected with HIV-1/BaL (300 $CCID_{50}$/ml). The susceptibility determination used monocytes/macrophages isolated from PBMCs from normal donors by plastic adherence. Every 5 days cultures were fed with complete medium containing the appropriate compound concentrations. The p24 antigen production was measured at day 14 after virus challenge and $EC_{50}$ and $EC_{90}$ values were calculated.

Recombinant Virus Assays

A recombinant virus assay (RVA) starts with the amplification of viral target sequences by means of PCR. The amplicons are incorporated into a proviral laboratory clone deleted for the sequences, present in the amplicon. This generates a stock of recombinant viruses. The viruses are tested for their ability to grow in the presence of different concentrations of drugs. Results are obtained by calculating $EC_{50}$ values for each inhibitor and by reporting the results as $EC_{50}$ values, expressed in µM concentrations, or by computing the ratio of the $EC_{50}$ values found for the recombinant virus to the $EC_{50}$ values found for a wild type susceptible laboratory virus tested in parallel. In the latter case, resistance is expressed as "fold-resistance" (fold change in susceptibility, FC) compared to a wild-type susceptible HIV-1 strain.

The use of reporter gene systems for susceptibility testing allows the implementation of laboratory automation and standardization (Pauwels, et al., J. Virol. Methods 20, 309-321 (1988); Paulous, S., et al., International Workshop on HIV Drug Resistance, Treatment Strategies and Eradication, St. Petersburg, Fla., USA. Abstr. 46 (1997); and Deeks, S. G., et al., 2nd International Workshop on HIV Drug Resistance and Treatment Strategies, Lake Maggiore, Italy. Abstr. 53 (1998)).

The Antivirogram® assay (Virco) (WO 97/27480) is based on homologous recombination of patient derived HIV-1 gag/PR/RT sequences into a proviral HIV-1 clone correspondingly deleted for the gag/PR/RT sequences. A similar assay (Phenosense® ViroLogic, WO 97/27319) is based on enzymatic ligation of patient-derived PR/RT sequences into a correspondingly deleted proviral vector carrying an indicator gene, luciferase, inserted in the deleted HIV-1 envelope gene. An other assay is developed by Bioalliance (Phenoscript, e.g. WO 02/38792). The development of high-throughput phenotyping and genotyping assays has allowed the establishment of a database containing the phenotypic resistance data and the genotypic sequences of over 30,000 clinical isolates.

EXPERIMENTAL PART

Example 1

The Identification of Mutational Patterns in HIV-1 Reverse Transcriptase and the Correlated Phenotypic Resistance Plasma samples from HIV-1-infected individuals from routine clinical practice were obtained and shipped to the laboratory on dry ice and stored at −70° C. until analysis. Viral RNA was extracted from 200 µL patient plasma using the QIAAMP® Viral RNA Extraction Kit (Qiagen, Hilden, Germany), according to the manufacturers instructions. cDNA encompassing part of the pol gene was produced using Expand™ reverse transcriptase (Boehringer Mannheim). A 2.2 kb fragment encoding the protease and RT regions were amplified from patient-derived viral RNA by nested polymerase chain reaction (PCR) using PCR primers and conditions as described. (Hertogs K., et al., Antimicrob. Agents Chemother. 42: 269-276 (1998), WO 01/81624). This genetic material was used in phenotyping and genotyping experiments.

Phenotypic analysis was performed using the recombinant virus assay (Antivirogram®)(WO 97/27480). MT-4 cells (Harada S., et al, Science 229: 563-566 (1985).) were co-transfected with pol gene PCR fragments and the protease-RT deleted HIV-1 molecular clone, pGEM3ΔPRT. This resulted in viable recombinant viruses containing protease/RT from the donor PCR fragment. After homologous recombination of amplicons into a PR-RT deleted proviral clone, the resulting recombinant viruses were harvested, titrated and used for in vitro susceptibility testing to antiretroviral drugs. The results of this analysis were expressed as fold change in susceptibility, reflecting the fold change in mean $EC_{50}$ (µM) of a particular drug when tested with patient-derived recombinant virus isolates, relative to the mean $EC_{50}$ (µM) of the same drug obtained when tested with a reference wild-type virus isolate (IIIB/LAI).

Genotyping was performed by an automated population-based full-sequence analysis, through a dideoxynucleotide-based approach, using the BigDye™ terminator kit (Applied Biosystems, Inc.) and resolved on an ABI 377 DNA sequencer.

The genotypes are reported as amino acid changes at positions along the reverse transcriptase gene compared to the wild-type (HXB2) reference sequence. Analysis by Virtual-Phenotype™ interpretational software (WO 01/79540) allowed detection of mutational patterns in the database containing the genetic sequences of the clinical isolates and linkage with the corresponding resistance profiles of the same isolates.

Example 2

Susceptibility Analysis of HIV-1 Variants Constructed by Site-Directed Mutagenesis Mutations in the protease or RT coding region were created by site-directed mutagenesis, using the QuikChange® Site-Directed Mutagenesis Kit (STRATAGENE®), of a wild-type HXB2-D EcoRI-PstI restriction enzyme fragment, encompassing the HIV-1 pol gene and cloned into pGEM3 (Promega). All mutant clones were verified by DNA sequence analysis. PCR fragments were prepared from the mutated clones and the altered reverse transcriptase coding regions were transferred into HIV-1 HXB2-D by homologous recombination as described above. The susceptibility of these recombinant viruses to drugs was determined by the MT-4 cell CPE protection assay.

Example 3

In Vitro Selection of Resistant Strains

Table 1

Cells are infected at a high MOI (such as 1-50 $CCID_{50}$/cell), corresponding to >$10^9$ viral RNA copies/ml. These experiments have been designed to mimic the quasi-species variability that is observed in HIV infected individuals where $10^9$ to $10^{10}$ new viruses are produced daily with a mutation rate of $10^{-4}$ to $10^{-5}$. The infected MT4-LTR-EGFP cells are treated with inhibitors at 40, 200 nM, 1 µM and higher for a maximum of 30 days. The cultures are subcultivated and scored on virus-induced fluorescence and cytopathicity every 3-4 days. If full virus breakthrough (100% CPE) is observed the supernatants was collected and stored (new virus strain). If no full CPE was observed the cells were subcultivated and further grown in the presence of the same concentration compound till full virus breakthrough, with a maximum of 30 days. From the emerging virus populations a virus stock was grown in the absence of compounds and titrated. The sensitivities of the isolated strains to HIV-1 RT inhibitors were determined and the strains were genotyped.
Table 2.

MT4-LTR-EGFP cells were infected at a multiplicity of infection (MOI) of 0.01 to 0.001 $CCID_{50}$/cell in the presence of inhibitor. The cultures were sub-cultivated and scored microscopically on virus-induced fluorescence and cyto-pathogenicity every 3-4 days. The cultures were sub-cultivated in the presence of the same compound concentration until signs of virus replication were observed. The escaping virus was further cultivated in the presence of the same inhibitor concentration in order to enrich the population in resistant variants. If full virus breakthrough was observed the supernatant was collected and stored (new virus strain). Afterwards, the same virus was challenged with a higher compound concentration in order to select variants able to grow in the presence of as high as possible inhibitor concentrations. From the new viruses, a virus stock was grown in the absence of inhibitor.

In vitro drug selection experiments starting from wild-type HIV-1/LAI under pressure of compound 1, Efavirenz and Nevirapine have been performed. Table 1 and 2 show the genotypic and phenotypic characterization of the selected strains.

TABLE 1

Characterization of the strains isolated from HIV-1/LAI in the presence of compound 1

| Starting strain | | LAI | High MOI LAI |
|---|---|---|---|
| Compound | | — | Compound 1 |
| Concentration (µM) | | | 0.200 µM |
| Days to breakthrough | | | day 25 |
| Original mutations | | | |
| Additional mutations | | | L100L/1 |
| | | | Y181C |
| | | | T386A |
| Phenotype | | | |
| Compound name | | | |
| Compound 1 | median (EC50 (µM)) | 0.0014 | 0.1097 |
| | Fold resistance | 1 | 78 |
| Efavirenz | median (EC50 (µM)) | 0.0010 | 0.2075 |
| | Fold resistance | 1 | 208 |

TABLE 2

Characterization of the strains isolated from HIV-1/LAI in the presence of compound 1

| | | Titer | | | | | | | |
|---|---|---|---|---|---|---|---|---|---|
| | | Low MOI | Low MOI | Low MOI | Low MOI | Low MOI | Low MOI | Low MOI | Low MOI |
| | | | | | | Viral strain | | | |
| | | LAI | LAI | LAI | LAI | LAI | LAI | LAI | LAI |
| | | | | | | Compound | | | |
| | | Comp. 1 | Comp. 1 | Comp. 1 | Comp. 1 | Comp. 1 | Comp. 1 | Comp. 1 | Comp. 1 |
| | | | | | | Concentration | | | |
| | | 0.040 µM | 0.200 µM | 0.200 µM | 1.000 µM | 5.000 µM | 5.000 µM | 15.000 µM | 15.000 µM |
| | | | | | | Days to breakthrough | | | |
| | | day 15 | day 22 | day 28 | day 35 | day 35 | day 42 | day 42 | day 59 |
| | | | | | | Mutations | | | |
| | | | | | | | | | I031L |
| | | | | M164M/I | | | I031L/I | I031L | A062A/V |
| | | | E006E/K | Y181C | | I031L/I | F116F/L | A062A/V | L074L/V |
| | | | Y181C | D186D/N | Y181C | Y181C | Y181C | Y181C | Y181C |
| | | Y181C | M230I | M230M/I | G190E | G190E | G190E | G190E | G190E |
| | | T386A | T386A | T386A | T386A | T386A | T386A | T386A | T386A |
| Compound 1 | median(EC50 (µM)) | 0.0014 | 0.0334 | 0.0298 | 0.0228 | 0.2168 | 0.3943 | 0.1263 | 0.6177 | >10.0000 |
| | Fold resistance | 1 | 24 | 21 | 16 | 155 | 282 | 90 | 441 | >7,143 |
| Efavirenz | median(EC50 (µM)) | 0.0010 | 0.0067 | 0.0067 | 0.0072 | 0.0465 | — | 0.0442 | 0.2086 | >10.0000 |
| | Fold resistance | 1 | 7 | 7 | 7 | 46 | — | 44 | 209 | >10,000 |
| Nevirapine | median(EC50 (µM)) | 0.0763 | >10.0000 | >10.0000 | >10.0000 | >10.0000 | >10.0000 | >10.0000 | >10.0000 | >10.0000 |
| | Fold resistance | 1 | >131 | >131 | >131 | >131 | >131 | >131 | >131 | >131 |

The in vitro antiviral activity of compound 1 and current reverse transcriptase inhibitors against the selected strains was evaluated in acutely infected MT4 cells. Median $EC_{50}$ values together with the fold change in resistance (expressed as a ration of $EC_{50}$) as compared to wild type (FC) are reported.

The invention claimed is:

1. A method of evaluating the relative effectiveness of drugs against mutant HIV reverse transcriptase comprising at least one mutation T386A, comprising the steps of:
   (i) providing a HIV reverse transcriptase comprising at least one mutation T386A, said position number is with reference to the HIV strain IIIB/LAI;
   (ii) determining the activity of said drugs on said mutant HIV reverse transcriptase;
   (iii) determining the activity of said drugs on a corresponding wild type HIV reverse transcriptase;
   (iv) determining the ratio of the activity determined in step (iii) over the activity determined in step (ii) for each drug; and
   (v) evaluating the relative effectiveness of the drugs against said mutant HIV reverse transcriptase based on the ratio of step (iv).

2. A method for evaluating a change in drug effectiveness against mutant HIV reverse transcriptase comprising at least one mutation T386A compared to wild type HIV reverse transcriptase, comprising the steps of:
   (i) providing a HIV reverse transcriptase comprising at least one mutation T386A, said position number is with reference to the HIV strain IIIB/LAI;
   (ii) determining the activity of said drug on said mutant HIV reverse transcriptase;
   (iii) determining the activity of said drug on a corresponding wild type HIV reverse transcriptase;
   (iv) determining the ratio of the activity determined in step (iii) over the activity determined in step (ii); and
   (v) identifying a change in drug effectiveness against said mutant HIV reverse transcriptase compared to said wild type based on the ratio of step (iv), wherein a ratio other than 1 is indicative of a change in effectiveness.

3. The method of claim 1, wherein the activity is measured as $EC_{50}$.

4. The method of claim 1, wherein the activity is measured as $EC_{90}$.

5. The method of claim 2, wherein the activity is measured as $EC_{50}$.

6. The method of claim 2, wherein the activity is measured as $EC_{90}$.

* * * * *